United States Patent
Zhu et al.

(10) Patent No.: US 11,684,593 B2
(45) Date of Patent: *Jun. 27, 2023

(54) APPLICATIONS OF SPERMINE AND ITS DERIVATIVE IN PREPARATION OF ANTITUMOR DRUG

(71) Applicant: GENEHEAL BIOTECHNOLOGY CO., LTD., Guangdong (CN)

(72) Inventors: Wei Zhu, Guangdong (CN); Wuguang Pan, Guangdong (CN)

(73) Assignee: Geneheal Biotechnology Co., Ltd., Guangzhou (CN)

(*) Notice: Subject to any disclaimer, the term of this patent is extended or adjusted under 35 U.S.C. 154(b) by 179 days.

This patent is subject to a terminal disclaimer.

(21) Appl. No.: 16/497,305

(22) PCT Filed: Feb. 6, 2018

(86) PCT No.: PCT/CN2018/075427
§ 371 (c)(1),
(2) Date: Sep. 24, 2019

(87) PCT Pub. No.: WO2018/192293
PCT Pub. Date: Oct. 25, 2018

(65) Prior Publication Data
US 2020/0330402 A1    Oct. 22, 2020

(30) Foreign Application Priority Data
Apr. 20, 2017 (CN) .......................... 201710261440.6

(51) Int. Cl.
*A61K 31/132* (2006.01)
*A61P 35/00* (2006.01)
*A61K 45/06* (2006.01)

(52) U.S. Cl.
CPC ............ *A61K 31/132* (2013.01); *A61P 35/00* (2018.01); *A61K 45/06* (2013.01)

(58) Field of Classification Search
CPC .............................. A61K 31/132; A61P 35/00
See application file for complete search history.

(56) References Cited

U.S. PATENT DOCUMENTS 4,952,585 A    8/1990   Sunkara et al.
5,541,230 A    7/1996   Basu et al.
(Continued)

FOREIGN PATENT DOCUMENTS

CN    101037423 A    9/2007
CN    101189002 A    5/2008
(Continued)

OTHER PUBLICATIONS

Li et al.; "Synthesis and Biological Evaluation of Novel Aromatic Imide-Polyamine Conjugates"; 2016; Molecules; 21:1637; doi: 10.3390/molecules21121637; pp. 1-16 (Year: 2016).*
(Continued)

*Primary Examiner* — Timothy P Thomas
(74) *Attorney, Agent, or Firm* — Fish & Richardson P.C.

(57) ABSTRACT

Applications of spermine or its pharmaceutically acceptable derivative in preparation of an SAICAR synthetase activity interfering agent or inhibitor. Applications of spermine or its pharmaceutically acceptable derivative in preparation of antitumor drug.

14 Claims, 4 Drawing Sheets

Control (no spermine)    Experimental group (with spermine)
(MYC is significantly inhibited)

(56) References Cited

U.S. PATENT DOCUMENTS

| | | | |
|---|---|---|---|
| 10,709,676 | B2 | 7/2020 | Pan et al. |
| 2004/0242701 | A1 | 12/2004 | Lojo et al. |
| 2012/0322877 | A1 | 12/2012 | Casero et al. |
| 2016/0369281 | A1 | 12/2016 | He |
| 2019/0209493 | A1 | 7/2019 | Pan et al. |
| 2019/0209499 | A1 | 7/2019 | Pan et al. |
| 2020/0297660 | A1 | 9/2020 | Pan et al. |

FOREIGN PATENT DOCUMENTS

| | | | |
|---|---|---|---|
| CN | 101205555 | | 6/2008 |
| CN | 103748091 | | 4/2014 |
| CN | 1829496 | | 5/2014 |
| CN | 104918611 | | 9/2015 |
| CN | 105246509 | | 1/2016 |
| CN | 106399380 | | 2/2017 |
| EP | 0270349 | | 6/1988 |
| EP | 3613416 | | 2/2020 |
| JP | 2001-172244 | | 6/2001 |
| WO | 9711691 A1 | | 4/1997 |
| WO | WO-9711691 A1 * | | 4/1997 ............ A61K 31/13 |
| WO | WO 1999/051213 | | 10/1999 |
| WO | WO 2003/037371 | | 5/2003 |
| WO | WO 2014/067038 | | 9/2006 |
| WO | WO 2009/151569 | | 12/2009 |
| WO | WO 2013/045826 | | 4/2013 |
| WO | WO 2014/075187 | | 5/2014 |
| WO | WO 2014/117272 | | 8/2014 |
| WO | WO 2018/059211 | | 4/2018 |
| WO | WO 2018/059212 | | 4/2018 |
| WO | WO 2018/059395 | | 4/2018 |
| WO | WO 2018/059396 | | 4/2018 |
| WO | WO 2018/192293 | | 10/2018 |

OTHER PUBLICATIONS

Chakravarthi et al.; "Expression and Role of PAICS, a De Novo Purine Biosynthetic Gene in Prostate Cancer"; Aug. 22, 2016; The Prostate; 77:10-21; DOI 10.1002/pros.23243 (Year: 2016).*
AU Office Action in Australian Appln. No. 2018253671, dated Jun. 18, 2020, 4 pages.
AU Office Action in Australian Appln. No. 2018253671, dated Mar. 17, 2020, 5 pages.
Chipperfiel et al., "Effects on the Activity of the Enzyme Phosphoribosyl Aminoimidazole Carboxylase, Involved in the Biosynthesis of the statural substrate 5- Amino-1-P-D-Ribofuranosylimidazole-4-Carboxylic Acid 5'-Phosphate," Nucleosides and Nucleotides, 1988, 7(5&6):571-576.
DrugBank.ca [Online]. "Spermine—ID DB00127," Jun. 2005, retrieved on Aug. 27, 2020, retrieved from URL<https://www.dragbank.ca/drugs/DB00127>, 11 pages.
EP Office Action in European Appln. No. 17854661.0-1112, dated May 20, 2020, 8 pages.
Horig et al., "From bench to clinic and back: Perspective on the 1st IQPC Translational Research conference," Journal of Translational Medicine, 2004, 2(44): 1-8.
Jaeken et al., "An infantile autistic syndrome characterized by the presence of succinylpurines in body fluids," The Lancet, 1984, 324(8411):1058-1061.
JP Office Action in Japanese Appln. No. 2019516530, dated Feb. 6, 2020, 10 pages (with English Translation).
JP Office Action in Japanese Appln. No. 2019516530, dated May 2, 2020, 10 pages (with English Translation).
JP Office Action in Japanese Appln. No. 2019551698, dated Jul. 17, 2020, 10 pages (with English Translation).
Jurecka et al., "Adenylosuccinate Lyase Deficiency," J. Inherit. Metab. Dis., 2015, 38(2):231-242.
Jurecka et al., "Clinical, biochemical and molecular findings in seven Polish patients with adenylosuccinatelyase deficiency," Mol Genet Metab. 2008, 94(4):435-442.
Mackenzie et al., "Synthesis of Analogues of 5-Aminoimidazole Ribonucleotides and their Effects as Inhibitors and Substrates of the Enzymes, Phosphoribosylaminoimidazole Carboxylase and Phosphoribosylaminoimidazolesuccinocarboxamide Synthetase Involved in the Biosynthesis of Purine Nucleotides de nova," Journal of the Chemical Society, Chemical Communications, 1976, 12:453-455.
Miller-Fleming et al., "Remaining Mysteries of Molecular Biology: The Role of Polyamines in the Cell," Journal of Molecular Biology, 2015, 427(21):3389-3406.
PCT International Preliminary Report on Patentability in International Appln. No. PCT/CN2017/101059, dated Apr. 2, 2019, 15 pages (with English Translation).
PCT International Preliminary Report on Patentability in International Appln. No. PCT/CN2018/075427, dated Oct. 22, 2019, 17 pages (with English Translation).
PCT International Search Report and Written Opinion in International Appln. No. PCT/CN2017/101059, dated Nov. 22, 2017, 22 pages (with English Translation).
PCT International Search Report and Written Opinion in International Appln. No. PCT/CN2018/075427, dated Mar. 28, 2018, 17 pages (with English Translation).
Peeg, "The Function of Spermine," IUBMB Life, 2014, 66(1):8-18.
Pharmacia, 1995, 31(4):373-377, with English Abstract.
Schafer et al.. "Failure Is an Option: Learning From Unsuccessful Proof-Of-Concept Trials," Drug Discovery Today, 2008, 13(21/22):913-916.
SG Office Actiorr in Singapore Appln. No. 1201908662X, dated Jan. 6, 2020, 7 pages.
Soda et al., "Increased Polvamine Intake Inhibits Age-Associated Alteration in Global DNA Methvlation and 1,2-Dimethylhydrazine-Induced Tumorigenesis," PlosOne, 2013, 8(5):e64357, 7 pages.
Van Den Bergh F et al., "Residual adenylosuccinase activities in fibroblasts of adenylosuccinase-deficient children: parallel deficiency with adenylosuccinate and succinyl-AICAR in profoundly retarded patients and non parallel deficiency in a mildly retarded girl," J. Inherit. Metab. Dis., 1993, 16(2):415-424.
Zikanova et al., "Preparation of 5-amino-4-imidazole-N-succinocarboxamide ribotide, 5-amino-4-imidazole-N-succinocarboxamide riboside and succinyladenosine, compounds usable in diagnosis and research of adenylosuccinate lyase deficiency," Journal of Inherited Metabolic Disease, 2005, 28(4):493-499.
Hanahan, D.and R.A. Weinberg, "Hallmarks of cancer: the next generation". Cell, 2011.144(5): p. 646-674.
Hsu, P.P. and D.M. Sabatini, Cancer cell metabolism: Warburg and beyond. Cell, 2008.134(5): p. 703-707.
Christofk, H.R., et al., The M2 splice isoform of pyruvate kinase is important for cancer metabolism and tumour growth. Nature, 2008. 452(7184): p. 230-233.
Wolf, A., et al., Hexokinase 2 is a key mediator of aerobic glycolysis and promotes tumor growth in human glioblastoma multiforme. J Exp Med, 2011,208(2): p. 313-326.
Chen, J., et al., Shikonin and its analogs inhibit cancer cell glycolysis by targeting tumor pyruvate kinase-M2. Oncogene, 2011.30(42): p. 4297-4306.
Anastasiou, D., et al., Pyruvate kinase M2 activators promote tetramer formation and suppress tumorigonesis. Nat Chem Biol, 2012.8(10): p. 839-847.
Vander Heiden, M.G., Exploiting tumor metabolism: challenges for clinical translation. J Clin Invest, 2013.123(9): p. 3648-3651.
Ciardo, F., C.Salerno, and P. Curatolo, Neurologic aspects of adenylosuccinate lyase deficiency. J Child Neurol, 2001.16(5): p. 301-308.
Gitiaux, C., et al., Misleading behavioural phenotype with adenylosuccinate lyase deficiency.Eur J Hum Genet, 2009.17(1): p. 133-136.
Mierzewska, H., et al., Severe encephalopathy with brain atrophy and hypomyelination due to adenylosuccinate lyase deficiency—MRI, clinical, biochemical and neuropathologicai findings of Polish patients. Folia Neuropathol, 2009.47(4): p. 314-320.
Eissmann, M., et al., A functional yeast survival screen of tumor-derived cDNA libraries designed to identify anti-apoptotic mammalian oncogenes. PLoS One, 2013.8(5), e64873: p. 1-16.

(56) References Cited

OTHER PUBLICATIONS

Goswami, M.T., et al., Role and regulation of coordinately expressed de novo purine biosynthetic enzymes PPAT and PAICS in lung cancer. Oncotarget, 2015.6(27); p. 23445-23461.
Chakravarthi, B.V., et al., Expression and Role of PAICS, a De Novo Purine Biosynthetic Gene in Prostate Cancer. Prostate, 2017. 77(1); p. 10-21.
Keller, K.E., I.S. Tan, and Y.S. Lee, SAICAR stimulates pyruvate kinase isoform M2 and promotes cancer cell survival in glucose-limited conditions. Science, 2012.338(6110): p. 1069-1072.
Keller, K.E., et al., SAICAR induces protein kinase activity of PKM2 that is necessary for sustained proliferative signaling of cancer cells. Mol Cell, 2014.53(5): p. 700-709.
Spiegel, E.K., Colman, R.F., and Patterson, D. (2006). Adenylosuccinate lyase deficiency. Mol Genet Metab 89, p. 19-31.
Clamadieu, C., Cottin, X., Rousselle, C., and Claris, O. (2008). Adenylosuccinate lyase deficiency: an unusual cause of neonatal seizure. Arch Pediatr 15, p. 135-138.
Castro, M., Perez-Cerda, C., Merinero, B., Garcia, M.J., Bemar, J., Gil Nagel, A., Torres, J., Bermudez, M., Garavito, P., Marie, S., et al., (2002). Screening for adenylosuccinate lyase deficiency; clinical, biochemical and molecular findings in four patients. Neuropediatrics 33, p. 186-189.
Criss W E. A Review of Polyamines and Cancer [J]. Turkish Journal of Medical Sciences, 2003, 33(4): p. 195-205.
Gerner E W, Meyskens FL Jr. Polyamines and cancer: old molecules, new understanding.[J]. Nat Rev Cancer. 2004, 4(10): p. 781-792.
Rial NS, Meyskens FL, Gerner EW. Polyamines as mediators of APC-dependent intestinal carcinogenesis and cancer chemoprevention [J]. Essays in biochemistry, 2009, 46(Suppl.1): p. 111-124.
Amendola R, Cervelli M, Fratini E, et al. Spermine metabolism and anticancer therapy[J]. Current cancer drug targets, 2009, 9(2): p. 118-130.
Mandal S, Mandal A, Johansson H E, et al. Depletion of cellular polyamines, spermidine and spermine, causes a total arrest in translation and growth in mammalian cells [J]. Proceedings of the National Academy of Sciences of the United States of America, 2013, 110(6): p. 2169-2174.
Pharmaceutical Salts: Properties, Selection and Use, P Heinrich Stahl (Editor), Camille G. Wermuth (Editor), ISBN: 3-90639-026-8, Hardcover, 388 pages, Aug. 2002.
U.S. Appl. No. 16/334,273, filed Mar. 18, 2018, U.S. Pat. No. 10,709,676, Pan et al.
U.S. Appl. No. 16/889,500, filed Jun. 1, 2020, Pan et al.
CA Office Action in Canadian Appln. No. 3057206, dated Mar. 31, 2021, 4 pages.
CA Office Action in Canadian Appln. No. 3057206, dated Oct. 23, 2020, 6 pages.
CA Office Action in Canadian Appln. No. 3064486, dated Mar. 12, 2021, 4 pages.
JP Notice of Allowance in Japanese Appln. No. 2019516530, dated Mar. 10, 2021, 5 pages (with English Translation).
JP Notice of Allowance in Japanese Appln. No. 2019551698, dated Nov. 20, 2020, 5 pages (with English Translation).
JP Office Action in Japanese Appln. No. 2019516530, dated Sep. 7, 2020, 8 pages (with English Translation).
KR Office Action in Korean Appln. No. 20197028417, dated Dec. 17, 2020, 15 pages (with English Translation).
Kuo et al., "A systems analysis of the chemosensitivity of breast cancer cells to the polyamine analogue PG-11047," BMC Medicine, Dec. 2009, 7:77, doi:10.1186/1741-7015-7-77, 11 pages.
Manjunath et al., "Catalytic pathway, substrate binding and stability in SAICAR synthetase: A structure and molecular dynamics study," Journal of Structural Biology, Jun. 2015, 191:22-31, http://dx.doi.org/10.1016/j.jsb.2015.06.006, 10 pages.
Ostanin et al., "Isolation and properties of phosphoribosyl succinocarboxamideaminoimidazole synthetase from the yeast Saccharomyces cerevisiae," Biokhimiia (Moscow, Russia), 1989, 54(8):1265-1273 (with English Abstract).
PCT International Preliminary Report on Patentability in International Appln. No. PCT/CN2017/101060, dated Apr. 2, 2019, 10 pages (with English Translation).
PCT International Preliminary Report on Patentability in International Appln. No. PCT/CN2017/101061, dated Apr. 2, 2019, 14 pages (with English Translation).
PCT International Preliminary Report on Patentability in International Appln. No. PCT/CN2018/078597, dated Oct. 22, 2019, 16 pages (with English Translation).
PCT International Preliminary Report on Patentability in International Appln. No. PCT/CN2018/078723, dated Oct. 22, 2019, 11 pages (with English Translation).
PCT International Search Report and Written Opinion in International Appln. No. PCT/CN2017/101060, dated Dec. 8, 2017, 16 pages (with English Translation).
PCT International Search Report and Written Opinion in International Appln. No. PCT/CN2017/101061, dated Nov. 28, 2017, 22 pages (with English Translation).
PCT International Search Report and Written Opinion in International Appln. No. PCT/CN2018/078597, dated Apr. 27, 2018, 24 pages (with English Translation).
PCT International Search Report and Written Opinion in International Appln. No. PCT/CN2018/078723, dated Jun. 5, 2018, 16 pages (with English Translation).
Tian, "Study on the Relationship between Autophagy and Viability Decrease of Hela Cells Induced by Spermidine," Abstract, China Master's Theses Full-text Database, Apr. 2013, 4 pages (with Machine Abstract).
Zhang et al., "Research Progress on Effect of Extrinsic Spermidine on Resistance of Organism," Chemistry and Bioengineering, Jul. 2015, 32(7):1-4, 4 pages (with Machine Abstract only).
Zhang, "Study on the Apoptosis of Hela Cells Induced by Spermidine," Abstract, China's Master's Theses Full-Text Database, Apr. 2013, 4 pages (with Machine Abstract).
AU Office Action in Australian Appln. No. 2018253689, dated Mar. 20, 2020, 4 pages.
EP Notice of Allowance in European Appln. No. 18787222.1, dated Jul. 20, 2021, 40 pages.
EP Office Action in European Appln. No. 18787222.1, dated Mar. 2, 2021, 6 pages.
EP Search Report in European Appln. No. 18788316.0, dated Dec. 15, 2020, 8 pages.
EP Search Report in European Appln. No. 18787222.1, dated Sep. 18, 2020, 9 pages.
KR Office Action in Korean Appln. No. 20197028417, dated Jun. 28, 2021, 10 pages (with English Translation).
Agarwal et al., "PAICS, a De Novo Purine Biosynthetic Enzyme, Is Overexpressed in Pancreatic Cancer and Is Involved in Its Progression," Translational Oncology, 2020, 13(7):100776, 10 pages.
Bhat et al., "Epidermal growth factor-induced prostate cancer (PC3) cell survival and proliferation is inhibited by quercetin, a plant flavonoid through apoptotic machinery," Biomedicine & Preventive Nutrition, 2014, 4:459-468.
CA Office Action in Canadian Appln. No. 3057206, dated Oct. 6, 2021, 3 pages.
CA Office Action in Canadian Appln. No. 3064486, dated Sep. 16, 2021, 3 pages.
Chakravarthi et al., "A Role for De Novo Purine Metabolic Enzyme PAICS in Bladder Cancer Progression," Neoplasia, 2018, 20(9):894-904.
KR Office Action in Korean Appln. No. 20197028417, dated Aug. 30, 2021, 7 pages (with English Translation).
Mao et al., "SATB1 is overexpressed in metastatic prostate cancer and promotes prostate cancer cell growth and invasion," Journal of Translational Medicine, 2013, 11:111.
Rokhlin et al., "Bcl-2 oncoprotein protects the human prostatic carcinoma cell line PC3 from TRAIL-mediated apoptosis" Oncogene, 2001, 20:2836-2843.
Song et al., "SIRPB1 promotes prostate cancer cell proliferation via Akt activation," Manuscript, The Prostate. 2020, 80(4):352-364.
Tan et al., "Knockdown of TRIM44 inhibits the proliferation and invasion in prostate cancer cells," Oncology Research, 2017, 25:1253-1259.

(56) References Cited

OTHER PUBLICATIONS

Zhou et al., "Roles of highly expressed PAICS in lung adenocarcinoma," Gene, 2019, 692:1-8.
Office Action in Chinese Appln. No. 201880019008.9, dated Mar. 9, 2022, 11 pages (with English translation).

* cited by examiner

Control (no spermine)  Experimental group (with spermine)
(MYC is significantly inhibited)

APPLICATIONS OF SPERMINE AND ITS DERIVATIVE IN PREPARATION OF ANTITUMOR DRUG

CROSS-REFERENCE TO RELATED APPLICATIONS

This application is the U.S. National phase of, and claims priority to, International Application No. PCT/CN2018/075427, filed Feb. 6, 2018, which designated the U.S. and which claims priority to Chinese Patent Application No. 201710261440.6, filed on Apr. 20, 2017. These applications are each incorporated herein by reference in their entireties.

TECHNICAL FIELD

The present disclosure relates to the use of a compound interfering with the activity of SAICAR synthetase, and particularly to the use of spermine and the derivatives thereof in the preparation of antitumor drug.

BACKGROUND ART

One important mark of cancer cells is metabolic reprogramming, including increased glucose uptake and oxygen-independent malolactic fermentation, which is also known as Warburg effect [1, 2], Such reprogramming is necessary for the growth and survival of tumors, especially under pressure conditions such as ambient hypoxia. However, it is still unclear for the important molecular mechanism, as well as the action mode for the correlation of the metabolic reprogramming of tumor cells with the rapid proliferation, differentiation, migration and the like of tumors.

Pyruvate kinase isoform M2 (PKM2), as one important enzyme in metabolic process, is highly expressed in most tumor cells which undergo rapid proliferation, and has great influence on the metabolism and growth of tumor cells [3, 4]. In addition, various pharmacological agents against PKM2 enzyme activity can affect the growth and proliferation of cells [5, 6]. It also suggests that altering tumor metabolism by targeting the enzyme activity of PKM2 would become a new approach for tumor therapy [7].

Purine metabolism is a ubiquitous and important biological metabolism in organisms. Its products. AMP and GMP, provide not only starting materials for the biosynthesis of DNA and RNA in the organisms, but also purine bases which are necessary for the in vivo synthesis of many key coenzymes (NAD, NADP, FAD and CoA), signal molecules (e.g. cAMP) and an important energy molecule ATP. It is thus evident that the purine metabolism is at the core position of the whole metabolic network. Purine synthesis comprises two synthetic pathways, i.e. de novo purine synthesis and salvage pathway.

In the adenine de novo synthesis pathway, adenylosuccinate lyase (hereinafter referred to as ADSL enzyme) mainly participates in the catalyzing and cleaving of SAICAR to form AICAR and in the generation of AMP from S-AMP [Spiegel, E. K., Colman, R. F., and Patterson, D. (2006). *Adenylosuccinate lyase deficiency*. Mol Genet Metab 89, 19-31. Clamadieu, C., Cottin, X., Rousselle, C., and Claris, O. (2008). *Adenylosuccinate lyase deficiency: an unusual cause of neonatal seizure*. Arch Pediatr 15, 135-138. Castro, M., Perez-Cerda, C., Merinero, B., Garcia, M. J., Bernar, J. Gil Nagel, A., Torres, J., Bermudez, M., Garavito, P., Marie, S., et al. (2002). *Screening for adenylosuccinate lyase deficiency: clinical, biochemical and molecular findings in four patients*. Neuropediatrics 33, 186-189].

In human bodies, abnormal metabolic enzyme in the adenine de novo synthesis pathway often leads to the accumulation of deleterious intermediate metabolite succinyl-5-aminoimidazole-4-carboxamide-1-ribose-5-phosphate (SAICAR), which has clinical symptoms such as autism, epilepsy, hypotonia, and dysplasia [8-10]. SAICAR synthase is encoded by gene PAICS (*phosphoribosylaminoimidazole succinocarboxamide synthetase/phosphoribosylaminotmiciazole carboxylase*), and is responsible for the synthesis of SAICAR in vivo. Related studies have reported that PAICS is highly expressed in acute lymphocytic leukemia, lung cancer, glioma prostate stage III colorectal cancer [11-13]. Recent studies have found that SAICAR can be highly accumulated under glucose-limited conditions, and would then alter energy level, sugar uptake, and generation of lactic acid in tumor cells. However, these phenomena are not found in adult epidermal cells and lung fibroblasts [14-15]. SAICAR can induce the enzymatic activity of PKM2 and promote the survival of tumor cells [14]. Moreover, the binding of SAICAR-PKM2 can induce the phosphorylation of Erk1/2, and SAICAR in high concentration can also induce the up-regulated expression of oncogene myc [15]. The accumulated SAICAR due to abnormal adenine de novo synthesis pathway promotes the proliferation and survival of tumor cells.

Phosphoribosylaminomidazole succinocarboxamidesynthetaseiphosphoribosylaminoimidazolecarboxylase, i.e. PAICS, is an important bifunctional enzyme in the purine de novo synthesis pathway, and has the functions of SAICAR synthetase (4-(N-succinylcarboxamide)-5-aminoimidazole ribonucleotidesynthetase, SAICARs) and AIR carboxylase (5-aminoimidazole ribonucleotidecarboxylase AIRc). PAICS catalyzes the sixth and seventh steps of the purine de novo synthesis, in which one key reaction process is shown as follows:

-continued

C00002

C00042  C00008  C00009

Therefore, tumors having abnormally high expression of PAWS are often accompanied by the accumulation of deleterious metabolite SAICAR. Researches on inhibiting the expression of PAWS or its enzymatic activity will become new means for tumor therapy. It is very important to develop or screen out compounds that can effectively inhibit the activity of PAICS.

Spermine (DrugBank ID: DB00127) is a polyamine-based compound containing two amino groups and two imino groups. Spermine is generated in vivo from putrescine (butanediamine) and S-adenosylmethionine through catalysis with various Spermine (DrugBank ID: DB00127) is a polyamine-based compound containing two amino groups and two imino groups Spermine is generated in vivo from pulrescine (bulanediamine) and S-adenosylmethionine through catalysis with various enzymes Spermine and spermidine are both present in bacteria and in most animal cells, find are important substances for promoting cell proliferation. Under acidic condition, it exhibits the characteristics of polycationic polyamines, and can bind with DNA in viruses and bacteria to make the DNA molecules more stable and flexible. It is also one of the necessary components in cell culture media Spermine is often overexpressed in tumor tissues, as disclosed by authoritative papers such as Criss W E. A Review of Polyamines and Cancer [J]. *Turkish Journal of Medical Sciences*, 2003, 33(4): 195-205. Gemer E W, Meyskens F L Jr. Polyamines and cancer, old molecules, new understanding.[J]. *Nat Rev Cancer.* 2004, 4(10): 781-792.; Rial N S. Meyskens F L, Gemer E W. Polyamines as mediators of APC-dependent intestinal carcinogenesis and cancer chemoprevention [J]. *Essays in biochemistry,* 2009. 46(Suppl.1): 111.; Amendola R. Cervelli M. Fratini E. et at. Spermine metabolism and anticancer therapy [J]. *Current cancer drug targets.* 2009. 9(2): 118-130.; Mandal S. Mandal A. Johansson H E. et al. Depletion of cellular polyamines, spermidine and spermine, causes a total arrest in translation and growth in mammalian cells [J]. *Proceedings of the National Academy of Sciences of the United States of America.* 2013, 110(6): 2169-74. It has long been known that spermine can promote the development of tumor cells and is a tumor promoter. Therefore, it is conductive to cancer-fighting by reducing the supply of spermine.

REFERENCES

1. Hanahan. D and R. A. Weinberg. *Hallmarks of cancer: the next generation.* Cell, 2011.44(5): p. 646-74.
2. Hsu, P. P. and D. M. Sabatini, *Cancer cell metabolism; Warburg and beyond.* Cell, 2008,134(5): p. 703-7.
3. Christofk. H. R., et al., *The M2 splice isoform of pyruvate kinase is important for cancer metabolism and tumour growth.* Nature. 2008.452(7184): p. 230-3.
4. Wolf. A. et al., *Hexokinase 2 is a key mediator of aerobic glycolysis and promotes tumor growth in human glioblastoma multiforme.* J Exp Med. 2011.208(2): p. 313-26.
5. Chen, J. et al., *Shikonin and its analogs Inhibit cancer cell glycolysis by targeting tumor pyruvate kinase-M2 Oncogene.* 2011.30(42): p. 4297-306
6. Anastasiou, D., et al., *Pyruvate kinase M2 activators promote tetramer formation and suppress tumorigenesis.* Nat Chem Biol. 2012 8(10): p. 839-47.
7. Vander Heiden. M. G., *Exploiting tumor metabolism: challenges for clinical translation.* J Clin Invest, 2013.123(9): p. 3648-51.
8. Ciardo. F., C. Salerno, and P. Curatolo. *Neurologic aspects of adenylosuccinate lyase deficiency.* J Child Neurol, 2001.16(5): p. 301-8.
9. Gitiaux. C., et al., *Misleading behavioural phenotype with adenylosuccinate lyase deficiency.* Eur J Hum Genet, 2009 17(1): p. 133-6.
10. Mierzewska. H. et al. *Severe encephalopathy with brain atrophy and hypomyelination due to adenylosuccinate lyase deficiency-MRI, clinical, biochemical and neuropathological findings of Polish patients.* Folia Neuropathol. 2009.47(4): p 314-20.
11. Eissmann, M., el al., *A functional yeast survival screen of tumor-derived cDNA libraries designed to identify anti-apoptotic mammalian oncogenes.* PLoS One, 2013.8 (5): p e64873.
12. Goswami. M. T., et al., *Role and regulation of coordinately expressed de novo purine biosynthetic enzymes PPAT and PAICS in lung cancer.* Oncotarget. 2015.6(27): p. 23445-61.
13. Chakravarthi. B. V., et al., *Expression and Role of PAICS, a De Novo Purine Biosynthetic Gene in Prostate Cancer.* Prostate. 2017.77(1): p. 10-21.
14. Keller, K. E., I. S. Tan, and Y. S. Lee, *SAICAR stimulates pyruvate kinase isoform M2 and promotes cancer cell survival in glucose-limited conditions.* Science, 2012.338 (6110): p. 1069-72.
15. Keller, K. E., et al., *SAICAR induces protein kinase activity of PKM2 that is necessary sustained proliferative signaling of cancer cells.* Mol Cell, 2014.53(5): p. 700-9.

SUMMARY OF THE INVENTION

An objective of the present disclosure is to provide use of spermine and derivatives thereof in the preparation of anti-tumor drugs.

The inventors, on the basis of existing data relating to the protein and small-molecule structures, performed calculation and analysis using software, and found that a compound with DrugBank ID DB00127 (general name: spermine) can effectively interfere with the activity of PAICS, and thus reduce SAICAR synthesis, thereby achieving the goal of treating or improving tumors.

The tumor may be one having any property selected from Warburg effect, high expression of oncogene myc, high expression of PAICS, being associated with Erk1/2, and high expression of PKM2 gene. In particular, the tumor may be selected from acute lymphocytic leukemia, lung cancer, glioma, prostate cancer, colorectal cancer, gastric cancer, liver cancer, esophageal cancer, colon cancer, malignant lymphoma, cervical cancer, nasopharyngeal cancer, breast cancer, skin cancer and bladder cancer, and especially be selected from acute lymphocytic leukemia, lung cancer, glioma, prostate cancer, and colorectal cancer which have the high expression of PAICS.

The meaning of "high expression" as used herein is well known in the art, and refers to the expression which is significantly increased as compared to that of normal tissues.

The pharmaceutically acceptable derivatives of the above compound may have the same parent core structure as the compound per se, and can produce molecules having the same or similar activity as the original compound through in vivo reactions such as hydrolysis and the like. Thus, the pharmaceutically acceptable derivatives can have the same or similar therapeutic effect as that of the original compound.

The pharmaceutically acceptable derivatives of the compound may particularly refer to simple derivatives thereof, especially to one of lower ester, lower ether, lower alkyl substituent, a medicinal salt, and lower amide thereof. That is, the pharmaceutically acceptable derivatives may be derivatives obtained by a condensation reaction between the parent compound with arboxylic acid, alcohol or amine having 1 to 6, preferably 2 to 6, and 2 to 4 carbon atom(s).

The pharmaceutically acceptable medicinal salt of the compound can be synthesized from the parent compound by a conventional chemical method, such as the method described in *Pharmaceutical Salts: Properties, Selection and Use*, P Heinrich Stahl (Editor), Camille G. Wermuth (Editor), ISBN: 3-90639-026-8, Hardcover, 388 pages, August 2002. In general, such salts can be prepared by reacting free alkali of the compound with an acid in water, an organic solvent or a mixed solution of both, generally in non-aqueous media such as diethyl ether, ethyl acetate, ethanol, isopropanol or acetonitrile.

The acid addition salt can be prepared using various acids (inorganic and organic acids). The examples of the acid addition salt may include salts prepared from acids, which may be selected from a group consisting of acetic acid, 2,2-dichloroacetic acid, adipic acid, alginic acid, ascorbic acid (e.g. L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (e.g. D-glucuronic acid), glutamic acid (e.g. L-glutamic acid), α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, metharie-sulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acids.

With combined utilization of at least two of the above compounds, it is expected to obtain better effect of treating and improving tumors.

BRIEF DESCRIPTION OF THE DRAWINGS

FIG. 3 shows the alignment result of the protein sequences of SAICAR synthetases from different species;

DETAILED DESCRIPTION OF THE EMBODIMENTS

Figure 1:
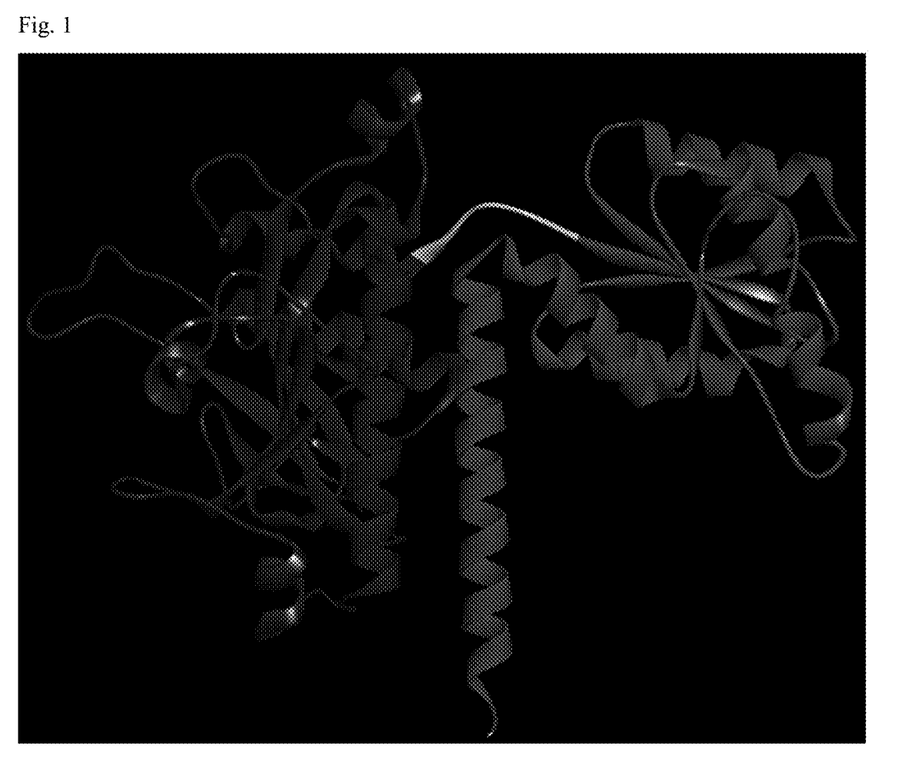
FIG. 1 shows the 3D solid ribbon structure diagram of PAICS.

There are 425 amino acid residues in the full length of the human PAICS protein sequence, in which 2-260AA is a SAICAR synthetase domain and 267-425 AA is AIR carboxylase domain, these two domains are linked by a peptide chain consisting of 6 amino acid residues (KSESQC). Furthermore, GLNI59-GLN183 α-helix in the SAICAR synthetase domain and ASN395-ASN424 α-helix in the AIR carboxylase domain interact with each other and are tightly bound together, as shown in FIG. 1.

SAICAR synthetase crystal structure data of different origins are collected in a protein structure database (RCSB), which includes *Saccharomyces cerevisiae* (1A48, 2CNQ, 2CNV, 2CNU, 10BD, 10BG), *Pyrococcushorikoshii* OT3 (3U54, 3U55), *Escherichia coil* (2GQR, 2GQS), *Methanocaldococcus jannaschii* (2YZL, 2Z02), *Streptococcus pneumonia* (4FGR, 4FE2), *Mycobacterium abscessus* ATCC 1977/DSM 44196 (3R9R), *Thermotoga maritime* (1KUT), *Clostridium perfringens* (3NUA), *Ehrlichia chaffeensis* (3KRE), *Geobacillus kaustophilus* (2YWV), as well as PAICS crystal structure data of *Homo sapiens* (2H31) and *Bombyx mori* (4JA0). Wherein, the complexes containing the structure of CAIR, are 2GQS, 2CNQ and 4FE2, and the complexes containing the structure of ASP are 2CNV, 2CNU and 4FE2.

Figure 2:
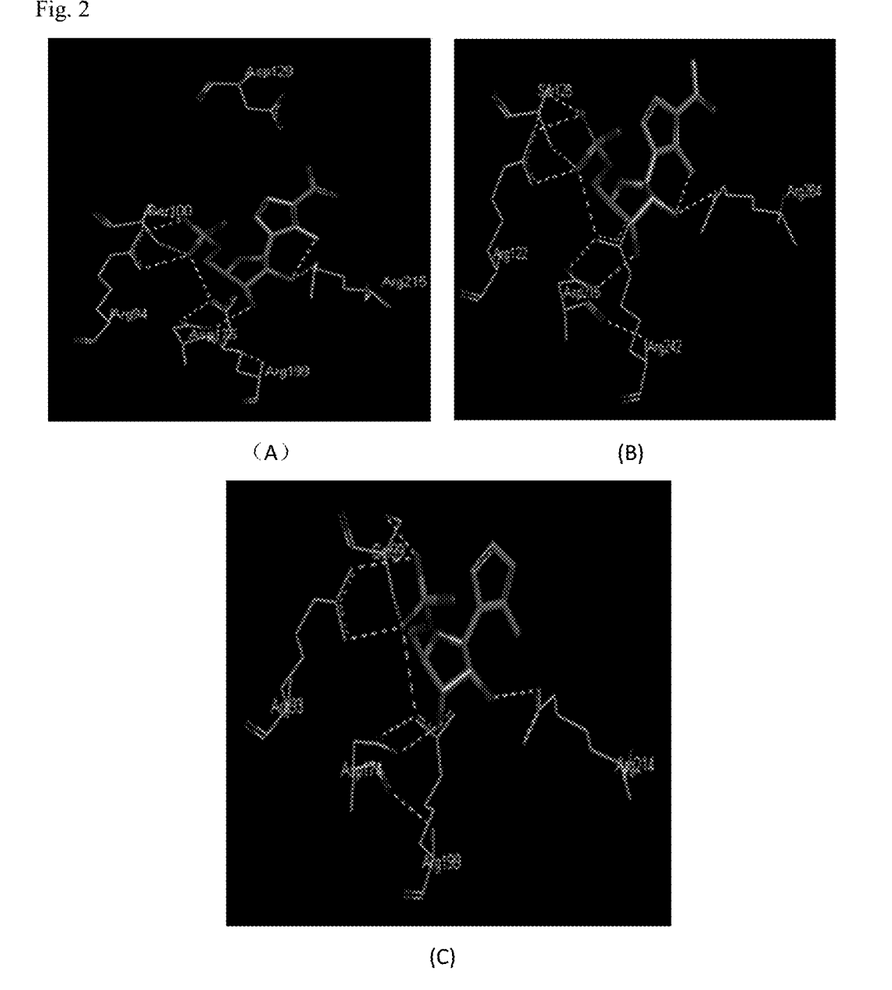
FIG. 2 shows the diagrams indicating the interaction of CAIR and SAICAR synthetase in the crystal structure, in which A: PDB access ID 2GQS; B: PDB access ID 2CNQ; and C: PDB access ID 4FE2.

As shown in FIG. 2, the residues within CAIR 3 Å in 2CNQ are Arg122, Ser128, ASP215, Arg242 and Arg264; the residues within CAIR 3 Å in 2G-QS are Arg94, Ser100, ASP129, ASP175, Arg199 and Ar 215; and the residues within CAIR 3 Å in 4FE2 are Arg93, Ser99, ASP174, Arg199 and Arg214. As can be seen from the alignment results of SAICAR protein sequences from different species (FIG. 3), it is highly conservative for the sequence, which binds with CAIR, of SAICAR synthetases from different species, and CAIR is primarily fixed by hydrogen bonds.

On the basis of the above results, the crystal structure conformations in SAICAR synthetases of *Saccharormyces cerevisiae* (PDB: 2CNQ) and *Escherichia coli* (PDB: 2GQS) are used as receptor structures for calculating and screening, since there is no conformation which can bind CAIR in human PAICS crystal structure, and is no catalytic conformation formed in the catalytic region, and the results obtained by calculation would be not reliable. 4661 of small molecule drugs in DrugBank (http://www.drugbank.ca/downloads#structures) are calculated and screened by using ligand fit module of Discovery studio.

The calculation results show that DB00127 (general name: Spermine) has a Dock Score of 316.723, indicating that the compound spermine can effectively interact with PAWS, and influence the synthesis of SAICAR.

Experimental Result Data of the Inhibition of Spermine PAWS Activity

It is confirmed by further biochemical enzyme activity experiments and cell biology experiments that the compound spermine can inhibit the accumulation of SAICAR up to 71.1%. The accumulation of toxic compound SAICAR is reduced by inhibiting the activity of PAICS.

Experimental Result Data of the Inhibition of Spermine on Oncogene MYC

Figure 4:
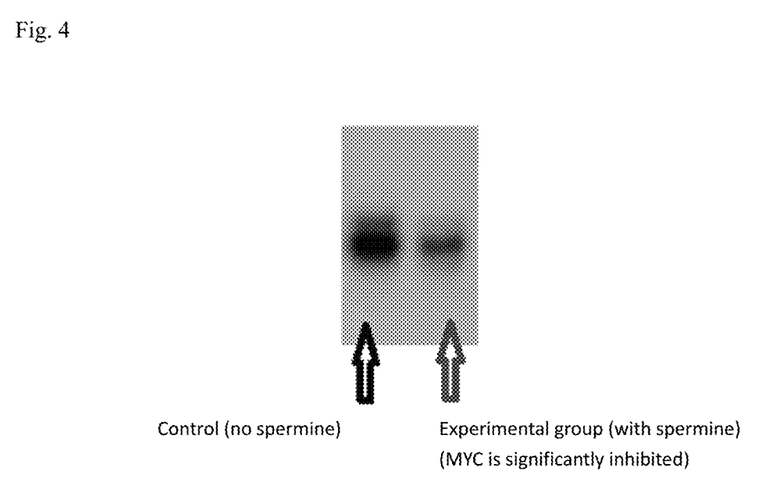
FIG. 4 shows the experimental result indicating the inhibition of spermine on oncogene MYC.

It is confirmed by further cell biology experiments and Western Blot experiments that the compound spermine can significantly inhibit the expression of oncogene my c, such that the expression of oncogene myc is significantly down-regulated (the results of Western Blot experiment are shown in FIG. 4).

Experimental Result Data of the Inhibition of Spermine on Cancer Cells

It is confirmed by further cell biology experiments that the compound spermine can effectively inhibit the growth of a lung cancer cell strain A549, a lung cancer cell strain H1299, a breast cancer cell strain MD468, and a breast cancer cell strain MD231 (the $IC_{50}$ values after 48 hours of drug administration are shown in table below), the anti-cancer effect is very significant.

| Cancer cell | IC50 (μM) |
|---|---|
| A549 | 117.317 |
| H1299 | 25.157 |
| MD468 | 38.027 |
| MD231 | 3.552 |

The above calculation data and experimental data fully indicate that spermine and pharmaceutically acceptable derivatives thereof can be developed as therapeutic drugs or health care products for tumors, especially tumor having any property selected from Warburg effect, high expression of oncogene myc, high expression of PAICS, being associated with Erk1/2 and high expression of PKM2 gene. In particular, the tumor may be selected from acute lymphocytic leukemia, lung cancer, glioma, prostate cancer, colorectal cancer, gastric cancer, liver cancer, esophageal cancer, colon cancer, malignant lymphoma, cervical cancer, nasopharyngeal cancer, breast cancer, skin cancer and bladder cancer. The tumor may especially be acute lymphocytic leukemia, lung cancer, glioma, prostate cancer, and colorectal cancer which have high expression of PAICS.

The pharmaceutically acceptable derivatives of the above compound have the same parent core structure as the compound per se, and can produce molecules having the same or similar activity as the original compound through in vivo reactions such as hydrolysis and the like. Thus, the pharmaceutically acceptable derivatives can have the same or similar therapeutic effect as that of the original compound.

The pharmaceutically acceptable derivatives of the compound particularly refers to simple derivatives thereof, especially to one of lower ester, lower ether, lower alkyl substituent, a medicinal salt, and lower amide thereof. That is, the pharmaceutically acceptable derivatives may be derivatives obtained by a condensation reaction between the parent compound with carboxylic acid, alcohol or amine having 1 to 6, preferably 2 to 6, and 2 to 4 carbon atom(s).

The pharmaceutically acceptable medicinal salt of the compound can be synthesized from the parent compound by a conventional chemical method, such as the method described in *Pharmaceutical Salts: Properties, Selection and Use*, P Heinrich Stahl (Editor), Camille G. Wermuth (Editor), ISBN: 3-90639-026-8, Hardcover, 388 pages, August 2002. In general, such salts can be prepared by reacting free alkali of the compound with an acid in water, an organic solvent or a mixed solution containing the both, generally in non-aqueous media such as diethyl ether, ethyl acetate, ethanol, isopropanol or acetonitrile.

The acid addition salt can be prepared using various acids (inorganic and organic acids). The examples of the acid addition salt includes salts prepared from acids, which may be selected from a group consisting of acetic acid, 2,2-dichloroacetic acid, adipic acid, alginic acid, ascorbic acid (e.g. L-ascorbic acid), L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, caloric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid (e.g. D-glucuronic acid), glutamic acid (e.g. L-glutamic acid), α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-by-droxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, suifocyanic acid, p-toluenesulfonic acid, undecylenic acid, pentanoic acid, and acylated amino acids.

It can improve, to a certain extent, the therapeutic effect and reduce the toxic and side effect by combined usage of drugs. Preferably, two, three, four, five or more compounds or derivatives thereof can be used simultaneously as the active ingredients for the treatment of tumors.

What is claimed is:

1. A method for treating or relieving a tumor, comprising administering a therapeutically effective amount of spermine or a pharmaceutically acceptable salt thereof to a patient in need of such treatment or relief;
   wherein the tumor is one having any property selected from the group consisting of high expression of oncogene myc, over expression of PAICS, and over-accumulation of SAICAR and the tumor is breast cancer or lung cancer.

2. The method according to claim 1, wherein the tumor can be improved due to the interference or inhibition of the activity of SAICAR synthetase.

3. The method according to claim 2, wherein the SAICAR synthetase is PAICS.

4. The method according to claim 1, wherein the method comprises administering spermine to the patient.

5. The method according to claim 1, wherein the method comprises administering a pharmaceutically acceptable salt of spermine to the patient.

6. The method according to claim 5, wherein the pharmaceutically acceptable salt is prepared from spermine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acids.

7. The method according to claim 1, wherein the tumor is breast cancer.

8. The method according to claim 7, wherein the method comprises administering spermine to the patient.

9. The method according to claim 7, wherein the method comprises administering a pharmaceutically acceptable salt of spermine to the patient.

10. The method according to claim 9, wherein the pharmaceutically acceptable salt is prepared from spermine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acids.

11. The method according to claim 1, wherein the tumor is lung cancer.

12. The method according to claim 11, wherein the method comprises administering spermine to the patient.

13. The method according to claim 11, wherein the method comprises administering a pharmaceutically acceptable salt of spermine to the patient.

14. The method according to claim 13, wherein the pharmaceutically acceptable salt is prepared from spermine and an acid selected from the group consisting of acetic acid, 2,2-dichloroacetic acid, adipic acid, alginic acid, ascorbic acid, L-aspartic acid, benzenesulfonic acid, benzoic acid, 4-acetylamino benzoic acid, butyric acid, (+)-camphoric acid, camphor sulfonic acid, (+)-(1S)-camphor-10-sulfonic acid, capric acid, hexanoic acid, octanoic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactonic acid, gentisic acid, glucoheptonic acid, D-gluconic acid, glucuronic acid, glutamic acid, α-ketoglutaric acid, glycolic acid, hippuric acid, hydrobromic acid, hydrochloric acid, hydroiodic acid, isethionic acid, (+)-L-lactic acid, (±)-DL-lactic acid, lactobionic acid, maleic acid, malic acid, (−)-L-malic acid, malonic acid, (±)-DL-mandelic acid, methanesulfonic acid, naphthalene-2-sulfonic acid, naphthalene-1,5-disulfonic acid, 1-hydroxyl-2-naphthoic acid, nicotinic acid, nitric acid, oleic acid, orotic acid, oxalic acid, palmitic acid, pamoic acid, phosphoric acid, propionic acid, L-pyroglutamic acid, salicylic acid, 4-aminosalicylic acid, sebacic acid, stearic acid, succinic acid, sulfuric acid, tannic acid, (+)-L-tartaric acid, sulfocyanic acid, p-toluenesulfonic acid, undecylenic acid, pentanoic acid, and acylated amino acids.

* * * * *

UNITED STATES PATENT AND TRADEMARK OFFICE
CERTIFICATE OF CORRECTION

| | |
|---|---|
| PATENT NO. | : 11,684,593 B2 |
| APPLICATION NO. | : 16/497305 |
| DATED | : June 27, 2023 |
| INVENTOR(S) | : Wei Zhu and Wuguang Pan |

It is certified that error appears in the above-identified patent and that said Letters Patent is hereby corrected as shown below:

In the Claims

Column 8, Line 48, Claim 1:
Delete "SAICAR" and Insert --SAICAR,--

Signed and Sealed this
Tenth Day of October, 2023

Katherine Kelly Vidal
*Director of the United States Patent and Trademark Office*